(12) United States Patent
Ollivier et al.

(10) Patent No.: US 7,862,721 B2
(45) Date of Patent: Jan. 4, 2011

(54) METHOD FOR PRODUCING HYDROGEN SULPHIDE AND THE USE THEREOF, IN PARTICULAR, FOR DEPOLLUTING HEAVY METAL-CONTAINING FLOWS

(75) Inventors: Bernard Marcel Noel Ollivier, Roquevaire (FR); Yannick Aman Baptiste Combet-Blanc, Marseilles (FR); Marie-Laure Fardeau, Les Pennes-Mirabeau (FR); Bruno Chardin, Aubagne (FR)

(73) Assignee: Institut de Recherche pour le Development (IRD), Paris (FR)

( * ) Notice: Subject to any disclaimer, the term of this patent is extended or adjusted under 35 U.S.C. 154(b) by 0 days.

(21) Appl. No.: 12/856,765

(22) Filed: Aug. 16, 2010

(65) Prior Publication Data

US 2010/0307985 A1   Dec. 9, 2010

Related U.S. Application Data

(62) Division of application No. 11/919,517, filed as application No. PCT/FR2006/000954 on Apr. 27, 2006, now Pat. No. 7,799,222.

(30) Foreign Application Priority Data

Apr. 29, 2005   (FR) .................................. 05 04386

(51) Int. Cl.
   *C02F 3/34* (2006.01)
(52) U.S. Cl. ..................... 210/603; 210/615; 210/631; 210/912
(58) Field of Classification Search ................. 210/603, 210/610, 615, 616, 617, 631, 912
   See application file for complete search history.

(56) References Cited

U.S. PATENT DOCUMENTS

| 4,108,722 A | 8/1978 | Stover |
| 4,522,723 A | 6/1985 | Kauffman |
| 4,789,478 A | 12/1988 | Revis |
| 5,062,956 A | 11/1991 | Lupton |
| 5,271,831 A | 12/1993 | Oremland |

(Continued)

FOREIGN PATENT DOCUMENTS

EP   0 692 458   1/1996

(Continued)

OTHER PUBLICATIONS

Pikuta E V et al., "*Desulfonatronum thiodismutans* sp. nov., a novel alkaliphilic, sufate-reducing bacterium capable of lithoautotrophic growth", 2003, pp. 1327-1332.

(Continued)

*Primary Examiner*—Fred Prince
(74) *Attorney, Agent, or Firm*—Young & Thompson (57) ABSTRACT

A process for the decontamination of an effluent containing one or more dissolved metals is provided. The process includes producing hydrogen sulphide in an aqueous medium by culturing alkaliphilic sulphate-reducing or thio-sulphate reducing bacteria in the presence of an organic compound serving as an electron donor and in the presence of a sulphurous compound serving as an electron acceptor. The effluent is contacted with the hydrogen sulphide and the dissolved metals are reduced and/or precipitated in the form of metal sulphides.

23 Claims, 5 Drawing Sheets

U.S. PATENT DOCUMENTS 5,587,079 A    12/1996   Rowley et al.
5,922,204 A *  7/1999    Hunter et al. ............... 210/603
6,315,904 B1   11/2001   Rose et al.
7,285,217 B2   10/2007   Simpson et al.

FOREIGN PATENT DOCUMENTS

WO    80/02281    10/1980
WO    97/05237    2/1997
WO    97/29055    8/1997
WO    02/06540    1/2002

OTHER PUBLICATIONS

Zhilina et al., *Desulfonatronovibrio hydrogenovorans* gen. nov. sp. nov., an alkaliphilic, sulphate reducing bacterium; Int. J. Syst. Bacteriol. Jan. 1997, p. 144.

* cited by examiner

METHOD FOR PRODUCING HYDROGEN SULPHIDE AND THE USE THEREOF, IN PARTICULAR, FOR DEPOLLUTING HEAVY METAL-CONTAINING FLOWS

This application is a divisional of application Ser. No. 11/919,517 filed on Dec. 13, 2007, now U.S. Pat. No. 7,799,222, which is the 35 U.S.C. §371 national stage of International PCT/FR20061000954 filed on Apr. 27, 2006, which claims priority to French Application No. 0504386 filed on Apr. 29, 2005. The entire contents of each of the above-identified applications are hereby incorporated by reference.

The invention relates to a process for the production of hydrogen sulphide and the use thereof, in particular for the decontamination of effluents containing heavy metals.

Heavy metals can be highly toxic to man and his environment. These heavy metals are not biodegradable, and hence they are of a cumulative nature. Thus more and more restrictive discharge standards have been imposed on industrial activities discharging metals.

The processes most commonly used to separate the heavy metals contained in industrial effluents utilise the formation of metal hydroxides. However, these processes do not always satisfy the current environmental standards relating to the acceptable levels of dissolved metals in effluents.

Another technology already in use involves the formation of metal sulphides. This requires the use of expensive synthetic polysulphides or the formation of gaseous hydrogen sulphide by the action of hydrochloric acid on sodium sulphide.

Biological alternatives to this mode of treatment, again involving the production of gaseous hydrogen sulphide, have been proposed in the past. These biological alternatives are based on two main types of biological mechanisms capable of leading to the formation of hydrogen sulphide:

1) The assimilative reduction of sulphate is an anabolic function which allows the majority of bacteria, fungi and plants to incorporate sulphur into amino acids (cysteine, methionine and cystine), vitamins (thiamine and biotin) and other sulphurous molecules (ferredoxin for example ...) present in the cells of these organisms. This reduction never leads directly to the production of hydrogen sulphide. Nonetheless, the latter is released indirectly during the fermentation of the proteinaceous organic matter.

2) The dissimilative reduction of sulphates is carried out by sulphate-reducing bacteria. In this anaerobic respiratory process, the sulphate is used as a terminal electron acceptor during the oxidation of hydrogen or of reduced organic compounds such as acetate and propionate. During this metabolism, the substrates are most often partially oxidised to acetate or, in some cases, totally oxidised resulting in the formation of $CO_2$.

Many patents or patent applications relate to the use of sulphate-reducing bacteria for the precipitation of metal ions as metal sulphides, in order to decontaminate effluents such as mine effluents or waste waters.

Thus, the documents WO 80/02281 and U.S. Pat. No. 4,522,723, relate to the use of bacteria of the *Desulfovibrio* or *Desulfotomaculum* type to reduce the levels of heavy metals in effluents. The document U.S. Pat. No. 4,108,722 envisages the injection of *Vibrio* and *Desulfovibrio* bacteria into contaminated subterranean aquifer reservoirs. The document U.S. Pat. No. 5,062,956 relates more specifically to hexavalent chromium treatment. Three other documents, U.S. Pat. No. 5,587,079, WO 97/29055 and WO 02/06540 propose other processes for biological precipitation of metals, with the distinctive feature that the precipitation is carried out sequentially, by varying the pH (mainly between 2.5 and 6.5) in order for example first to precipitate copper, then zinc etc. ... The document WO 97/05237, which discloses the use of methylotrophic bacteria, i.e. which are capable of using methanol as the sole source of carbon, may also be cited. It must also be noted that systems of co-culture of bacteria of different strains have also been envisaged, for example in the document U.S. Pat. No. 4,789,478 or the document EP 0 692 458.

A disadvantage of the processes cited above resides in the fact that sometimes considerable quantities of hydrogen sulphide in gaseous form ($H_2S$) are produced during these processes. This is particularly the case when it is desired to obtain maximal precipitation of the metals initially dissolved in the effluent to be decontaminated, which requires the use of the hydrogen sulphide in excess. Now hydrogen sulphide in gaseous form is toxic, corrosive, harmful to the environment and requires an appropriate supplementary restrictive treatment.

One way of avoiding this disadvantage consists in producing dissolved hydrogen sulphide (in the form of $HS^-$) instead of gaseous hydrogen sulphide. In order to do this, it is desirable that the pH of the culture solution in which the sulphide is produced by the sulphate-reducing bacteria be as high (basic) as possible. Now, in the great majority of the sulphate-reducing bacteria the use of a high pH adversely affects the sulphide production yield and can even be lethal to the culture.

One of the aspects of the invention is to produce essentially soluble hydrogen sulphide, in good yield, by means of sulphate- or thiosulphate-reducing bacteria.

One of the other aspects of the invention is to propose new culture conditions for certain sulphate-reducing bacteria, making it possible in particular to make use of their thiosulphate-reducing properties.

One of the other aspects of the invention is to propose a process for the decontamination of effluents containing heavy metals by means of hydrogen sulphide produced by the culturing of sulphate- or thiosulphate-reducing bacteria.

Yet another aspect of the invention is to produce hydrogen sulphide for the decontamination of effluents containing heavy metals, while avoiding the undesirable presence of gaseous hydrogen sulphide.

These different aspects are obtained by using certain recently discovered sulphate-reducing alkaliphilic bacteria, not until now used to produce hydrogen sulphide or a fortiori for the decontamination of effluents laden with metals.

The invention thus relates to the use of alkaliphilic sulphate-reducing or thiosulphate-reducing bacteria selected from at least one species of the Desulfohalobiaceae family or of the *Desulfonatronum* genus or of which the gene coding for the ribosomal RNA 16 S exhibits a homology of at least 97% with the corresponding gene of any one of the species of the Desulfohalobiaceae family or of the *Desulfonatronum* genus, to produce hydrogen sulphide in a form largely soluble in an aqueous medium.

By "alkaliphilic bacteria" is meant bacteria whose life, growth, and various metabolic and enzymatic activities preferably take place at a basic pH.

A taxonomic, morphological and physiological description of the bacteria used in the invention has been given in the following articles:

Pikuta et al., *Desulfonatronum lacustre gen. nov. sp. nov.: a new alkaliphilic sulphate-reducing bacterium utilizing ethanol*; Microbiology 67, 105;

Zhilina et al., *Desulfonatronovibrio hydrogenovorans gen. nov. sp. nov., an alkaliphilic, sulphate-reducing bacterium*; Int. J. Syst. Bacteriol. January 1997, p. 144;

Pikuta et al., *Desulfonatronum thiodismutans sp. nov., a novel alkaliphilic, sulphate-reducing bacterium capable of lithoautotrophic growth*; Int. J. Syst. Evol. Microbiol. 53, 1327.

"Homology" is used to designate the proportion of identity between two nucleic acid sequences. This homology can be measured by seeking to align the said sequences using an algorithm such as that defined in Altschul et al. (*Nucl. Acid Res.* 25:3389, 1997) or by using for example the software Clustal W, well known to the person skilled in the art and described in Thompson et al. (*Nucl. Acid Res.* 22:4673, 1994).

By "form largely soluble" is meant a ratio of soluble hydrogen sulphide produced to gaseous hydrogen sulphide produced greater than 1, and in particular greater than 100.

As will be described in detail below, for the conditions for culturing the sulphate-reducing bacteria according to the invention, novel substrates, namely formate and thiosulphate, are preferably used. The formate serves as an energy source, while the thiosulphate serves as an electron acceptor and source of sulphur: the strains of bacteria used in the invention are thus thiosulphate-reducing as well as being sulphate-reducing. This property of certain sulphate-reducing bacteria of utilising thiosulphate as a substrate has not been used in the previously cited processes for metal decontamination.

The use of alkaliphilic sulphate- or thiosulphate-reducing bacteria under the conditions of the invention makes it possible to produce hydrogen sulphide in a very largely soluble form, and in an exceptionally high yield.

Another decisive advantage of the invention is the possibility that it affords of working with a pure culture pure without having to perform any sterilisation, which makes considerable savings possible. In fact, the particular culture conditions which are used (high pH, mineral content, absence of $O_2$, high concentration of hydrogen sulphide . . . ) ensure a strong selection pressure.

Advantageously, the use of alkaliphilic sulphate-reducing or thiosulphate-reducing bacteria according to the invention is carried out at a pH greater than or equal to about 9, in particular at a pH greater than or equal to about 9.5, in particular at a pH greater than or equal to about 10.

The proportion of the hydrogen sulphide produced according to the invention which is in gaseous form (in other words the ratio of gaseous hydrogen sulphide produced to the dissolved hydrogen sulphide produced) in fact depends on the pH at which the hydrogen sulphide is produced. At an acidic pH, the predominant form of the hydrogen sulphide is the gaseous form. At a pH of 7 there are about as many molecules of $H_2S$ as $HS^-$ ions. At a pH of 9, the proportion of gaseous hydrogen sulphide is only about 1/100. At a pH of 9.5, the proportion of gaseous hydrogen sulphide is only about 1/500. At a pH of 10, the proportion of gaseous hydrogen sulphide is only about 1/1000.

According to another advantageous implementation of the invention, the use of alkaliphilic sulphate-reducing or thiosulphate-reducing bacteria takes place in the form of culturing in the presence of an organic compound serving as an electron donor, in particular formate, and in the presence of a sulphurous compound serving as an electron acceptor, in particular thiosulphate.

However, it is important to note that, depending on the bacterial strains utilised, other substrates can serve for the production of sulphide: for example sulphate, sulphite or sulphur as electron acceptor, and ethanol or dihydrogen as electron donor.

However that may be, the production of hydrogen sulphide is carried out in the invention via the reduction of a sulphurous compound. In the case where this sulphurous compound is thiosulphate ($S_2O_3^{2-}$), the enzymatic reduction mechanisms involved are in particular based on thiosulphate sulphur transferase (or rhodanese) and on thiosulphate reductase.

In the first case, the outcome of the thiosulphate reduction reaction is equivalent to an oxidation of a thiol group by the thiosulphate, the sulphonyl part of which is reduced to sulphite:

In the second case, the thiosulphate is cleaved to sulphite and sulphide, and the sulphite is then reduced to sulphide, with the final outcome:

Also a subject of the invention is a process for the production of hydrogen sulphide in a form largely soluble in an aqueous medium comprising:

a stage of culturing alkaliphilic sulphate-reducing or thiosulphate-reducing bacteria selected from at least one species of the Desulfohalobiaceae family or of the *Desulfonatronum* genus or of which the gene coding for the ribosomal RNA 16 S exhibits a homology of at least 97% with the corresponding gene of any one of the species of the Desulfohalobiaceae family or of the *Desulfonatronum* genus, in the presence of an organic compound serving as an electron donor, in particular formate, and in the presence of a sulphurous compound serving as an electron acceptor, in particular thiosulphate, which leads to the formation of hydrogen sulphide.

This bacterial culturing stage can for example be carried out in a standard reactor such as those available on the market for fermentation, on the pilot scale and on the industrial scale alike.

Advantageously, in the process for the production of hydrogen sulphide according to the invention, the culturing of the alkaliphilic sulphate-reducing or thiosulphate-reducing bacteria is carried out at a pH greater than or equal to about 9, in particular at a pH greater than or equal to about 9.5, in particular at a pH greater than or equal to about 10.

If necessary, the pH can be measured and regulated by the addition of acidic and/or basic substances.

According to a preferred implementation of the process for the production of hydrogen sulphide according to the invention, the bacteria are selected such that they display a tolerance to hydrogen sulphide, the said tolerance being characterised in that the bacteria tolerate concentrations of hydrogen sulphide at least greater than 20 mM.

By "tolerance" is meant the survival of the bacteria and the maintenance of normal metabolic activity, which can be observed by the consumption of the energy source.

This good tolerance of the bacteria in culture makes it possible to obtain solutions with a high concentration of hydrogen sulphide.

Advantageously, the bacteria used in the process for the production of hydrogen sulphide according to the invention belong to the species *Desulfonatronum lacustre*.

Advantageously, the bacteria used in the process for the production of hydrogen sulphide according to the invention belong to the species *Desulfonatronovibrio hydrogenevorans*.

According to an advantageous implementation of the invention, the culturing involved in the process for the production of hydrogen sulphide is carried out on a support suitable for the growth of the bacteria, leading to the formation of a biofilm.

By "biofilm" is meant bacteria preferentially immobilised on a suitable support, of the pozzolane, Cloisonyl®, Bio-Net® or Sessil® type for example, instead of a simple suspension of bacteria in solution. Culturing in biofilms makes it possible to obtain high concentrations of bacterial cells locally and to produce hydrogen sulphide more rapidly. Moreover, few bacterial cells are removed from the reactor during the withdrawal of the culture solution containing the hydrogen sulphide, since the bacteria are largely not in suspension.

According to a preferred implementation of the process for the production of hydrogen sulphide according to the invention, this comprises a sequence of the following two stages:

a first stage in which the culturing of the bacteria is carried out under conditions appropriate for the growth of the said bacteria and for the concomitant production of hydrogen sulphide, and a second stage in which the culturing of the bacteria is carried out under conditions appropriate for the production of hydrogen sulphide in the absence of growth of the said bacteria, it being possible to repeat several times the sequence of the said stages constituting one cycle if necessary.

By "growth of the said bacteria" is meant in particular their multiplication by cell division.

By "production of hydrogen sulphide in the absence of growth of the said bacteria" is meant on the one hand the substantial arrest or marked slowing of growth, in other words of the multiplication of the bacteria, but also on the other hand the survival of these bacteria or at least the maintenance of enzymatic activity of bacterial origin causing the formation of hydrogen sulphide in the medium.

Preferably, the passage from one of the said stages to the other is in particular carried out by means of addition of one or several acidic or basic chemical substances, causing a change in the pH of the bacterial culture medium.

Particularly preferably, the said first stage is carried out at a pH ranging from about 9 to about 10 and the said second stage is carried out at a pH greater than about 10.

In fact, the bacteria used in the invention are capable of maintaining their hydrogen sulphide production activity at particularly extreme alkaline pH, that is to say in particular at a pH greater than about 10. It is thus advantageous to culture the bacteria of the invention in an initial period at their optimal culture pH, which in general lies between about 9 and about 10, so as to obtain the greatest possible number of bacteria, then in a second period to pass to a pH greater than about 10 so as to continue to produce hydrogen sulphide, but under chemical conditions of the medium such that the ratio of the gaseous hydrogen sulphide produced to hydrogen sulphide produced is as low as possible, and in particular less than 1/100.

According to a preferred implementation of the invention, the hydrogen sulphide is produced at a concentration greater than or equal to about 10 mM, in particular at a concentration greater than or equal to about 20 mM, in particular at a concentration greater than or equal to about 30 mM, in particular at a concentration greater than or equal to about 40 mM.

The typical specific rate of production of hydrogen sulphide that can be attained according to the invention is at least 2.9 mmol $HS^-$ $g^{-1}$ $hr^{-1}$ and can range up to 5 mmol $HS^-$ $g^{-1}$ $hr^{-1}$.

According to another preferred implementation of the invention, the hydrogen sulphide is produced by a culture of bacteria belonging to the species *Desulfonatronum lacustre*, the organic compound serving as an electron donor being formate, and the sulphurous compound serving as an electron acceptor being thiosulphate, and the bacteria are continuously cultured on a biofilm at a pH greater than about 10.

Also a subject of the invention is a process for the decontamination of an effluent containing one or more dissolved metals comprising:

a stage of production of hydrogen sulphide in a form largely soluble in an aqueous medium by means of a culture of alkaliphilic sulphate-reducing or thiosulphate-reducing bacteria selected from at least one species of the Desulfohalobiaceae family or of the *Desulfonatronum* genus or of which the gene coding for the ribosomal RNA 16 S exhibits a homology of at least 97% with the corresponding gene of any one of the species of the Desulfohalobiaceae family or of the *Desulfonatronum* genus in the presence of an organic compound serving as an electron donor, in particular formate, and in the presence of a sulphurous compound serving as an electron acceptor, in particular thiosulphate, and a stage of contacting the said effluent with the hydrogen sulphide obtained in the preceding stage, resulting in the reduction of the said dissolved metals and/or the precipitation of the said dissolved metals in the form of metal sulphides, the said contacting being carried out at a pH ranging from about 2 to about 12.

By "decontamination of an effluent containing one or more dissolved metals" is meant the significant reduction of the concentration of one or more metals dissolved in the effluent, and in particular a reduction below the thresholds imposed by the various environmental standards for discharges.

Examples of thresholds for metal concentrations in liquid discharges currently imposed by French legislation are as follows: 0.5 mg/L for copper; 0.5 to 2 mg/L for zinc; 0.05 to 0.5 mg/L for arsenic; 0.05 to 0.2 mg/L for cadmium; 0.1 mg/L for hexavalent chromium; 0.5 to 2 mg/L for tin; 0.03 to 0.05 mg/L for mercury; 0.5 to 2 mg/L for nickel and 0.1 to 0.5 mg/L for lead. It must also be noted that the thresholds can vary depending on the industries involved, and that bylaws sometimes locally set thresholds up to 100 times lower than the values cited above.

Now, with the exception of the special case of chromium, almost all the metals can be precipitated as metal sulphides by the action of hydrogen sulphide and display lower solubility in the form of metal sulphides than in the form of metal hydroxides.

In fact the minimal solubilities observed, at various pH, for the metal hydroxides and sulphides are as follows:

$5.2 \times 10^{-2}$ mg/L for arsenic sulphide (and no formation of arsenic hydroxide);

$6.7 \times 10^{-10}$ mg/L for cadmium sulphide versus $2.3 \times 10^{-5}$ mg/L for cadmium hydroxide;

$1.0 \times 10^{-8}$ mg/L for copper sulphide versus $2.2 \times 10^{-2}$ mg/L for copper hydroxide;

$3.8 \times 10^{-8}$ mg/L for tin sulphide versus $1.1 \times 10^{-4}$ mg/L for tin hydroxide;

$2.1 \times 10^{-3}$ mg/L for manganese sulphide versus 1.2 mg/L for manganese hydroxide;

$9.0 \times 10^{-20}$ mg/L for mercury sulphide versus $3.9 \times 10^{-4}$ mg/L for mercury hydroxide;

$6.9 \times 10^{-8}$ mg/L for nickel sulphide versus $6.9 \times 10^{-3}$ mg/L for nickel hydroxide;

$3.8 \times 10^{-9}$ mg/L for lead sulphide versus 2.1 mg/L for lead hydroxide; and $2.3 \times 10^{-7}$ mg/L for zinc sulphide versus 1.1 mg/L for zinc hydroxide;

In the particular case of chromium in its hexavalent form, precipitation in the form of sulphide is not possible, but on the other hand the hydrogen sulphide makes it possible to reduce the $Cr^{6+}$ ion to the $Cr^{3+}$ ion (Kim et al. 2001, Chromium VI reduction by hydrogen sulfide in aqueous media: stoichiometry and kinetics. Environ. Sci. Technol. 35(11): 2219-2225), which is much less toxic and less soluble, particularly in its hydroxide form.

Further, the solubility of the metal hydroxides is generally minimal for a certain optimal pH value, whereas the solubility of the metal sulphides is typically a purely decreasing function of the pH, so that it is always advantageous, solely from the point of view of the solubility of the sulphides, to work at a pH as basic as possible.

In summary, the decontamination of effluents according to the invention is thus particularly advantageous compared to processes making use of a simple precipitation in the form of hydroxides for:
- arsenic, which cannot be insolubilised as hydroxide, and whose insolubilisation as sulphide makes it possible to observe the threshold values for discharge;
- hexavalent chromium, which cannot precipitate efficiently as hydroxide without having been previously reduced to trivalent chromium by the hydrogen sulphide; and
- manganese, zinc and lead, the precipitation of which as sulphides makes it possible to observe the threshold values for discharge, unlike the precipitation thereof as hydroxides.

Examples of effluents which can be treated according to the invention are: effluents from the chemical, chemistry-related and petroleum industries and in particular the coatings and pigment production industry; effluents from the mineral industry and in particular the glass industry (high discharge of lead); effluents from the engineering and surface treatment sector; effluents from the iron and steel and metallurgical sector (in particular for arsenic, chromium VI, lead and manganese discharges); and effluents from the waste materials treatment sector.

In the said process for the decontamination of an effluent containing one or more dissolved metals according to the invention, the hydrogen sulphide production stage can be carried out in any of the manners described above.

According to a preferred implementation of the said process for the decontamination of an effluent containing one or more dissolved metals, the stage of contacting the effluent with the hydrogen sulphide is carried out at a neutral or basic pH.

This implementation makes it possible to minimise any release of gaseous hydrogen sulphide during the contacting stage and enables more complete precipitation of the metal sulphides, which are less soluble at a high pH than at a low pH.

Advantageously, in the said process for the decontamination of an effluent containing one or more dissolved metals, the production of hydrogen sulphide and the contacting of the effluent with the hydrogen sulphide are carried out in separate tanks, in particular respectively a culturing tank and a reaction tank, the said process comprising an intermediate stage between the hydrogen sulphide production stage and the stage of contacting the effluent with the hydrogen sulphide, the said intermediate stage consisting in the injection of all or part of the hydrogen sulphide produced in the culturing tank into the reaction tank.

At the decontamination stage, in other words the contacting of the polluted effluent and all or part of the hydrogen sulphide produced, in the reaction tank, or after that said stage, it is possible to add coagulating agents such as $FeCl_3$, in order to cause flocculation of the insolubilised metal sulphides, then if necessary to pass the effluent into a lamellar decanter in order to separate the precipitates after sedimentation.

According to a particular implementation of the process for the decontamination of an effluent containing one or more dissolved metals according to the invention, a fraction of the effluent is injected into the culturing tank.

This implementation can be described as production "with contacting" or "with partial contacting" of the effluent. In cases where the composition of the effluent is such that the effluent does not significantly reduce the capacity for the production of hydrogen sulphide by the bacteria when these are cultured in contact with that effluent, this implementation can present an economic advantage.

According to another particularly preferred, implementation of the process for the decontamination of an effluent containing one or more dissolved metals according to the invention, no fraction of the effluent is injected into the culturing tank.

This implementation can be described as production "in parallel with" the effluent. It is particularly advantageous, since the bacteria destined to produce the hydrogen sulphide never come into contact with the polluted effluent; now such contacting can impair the hydrogen sulphide production capacity of the bacteria in a proportion which is difficult to forecast, depending on their better or worse resistance to the presence of dissolved metals in the culture medium.

Advantageously, the process for the decontamination of an effluent containing one or more dissolved metals according to the invention is such that the stage of contacting the effluent with the hydrogen sulphide in the reaction tank is carried out in the absence of a gaseous phase, so that there is no release of gaseous hydrogen sulphide.

By "in the absence of a gaseous phase" is meant: in the absence of any contact with air or any other gas. According to the established terminology, this contacting therefore takes place in a "flooded medium". This characteristic is advantageous inasmuch as a release of gaseous hydrogen sulphide is to be expected in the presence of a gaseous phase, and all the more since the pH in the reaction tank can be basic but also neutral or acidic, in which case the chemical equilibrium between dissolved hydrogen sulphide and gaseous hydrogen sulphide is displaced in favour of the latter.

It should be noted that in the other previously cited implementation modes of the decontamination process according to the invention, in case of the presence of a gaseous phase, the concentration of gaseous hydrogen sulphide possibly released during the contacting stage is preferably less than 5 $mg/m^3$.

As regards the culturing tank, this can contain a gaseous phase. In that case, the gaseous hydrogen sulphide possibly present in this gaseous phase can serve to reduce the oxidant compounds introduced into the medium. In case of gas overpressure, the gaseous hydrogen sulphide can be neutralised by washing with caustic soda (NaOH). In any case, the concentration of gaseous hydrogen sulphide released in the culturing tank is preferably less than 5 $mg/m^3$.

According to a preferred implementation of the invention, the aforesaid process for the decontamination of an effluent containing one or more dissolved metals comprises the supplementary stages of:
- measurement of the concentration of hydrogen sulphide produced in the culturing tank,
- estimation of the concentration of the metals or different metals dissolved in the effluent to be decontaminated, and adjustment of the quantity of solution containing hydrogen sulphide having to be injected into the reaction tank on the basis of the result of the said measurement and of the said estimation.

In other words, according to this implementation it is possible to use the process for the decontamination of an effluent according to the invention in various applications, that is to say it is possible to decontaminate effluents having vary diverse characteristics in terms of concentrations of dissolved metals, by a simple and immediate adaptation of the process of the invention. In fact it suffices to have available a sufficiently large production of hydrogen sulphide, then to adapt the quantity of hydrogen sulphide for contacting with the effluent to the nature of that effluent to be decontaminated.

Non-limiting examples of metal or metals dissolved in a polluted effluent that can be treated by means of the invention are: copper, zinc, arsenic, cadmium, chromium, particularly in its hexavalent form, tin, manganese, mercury, nickel, and lead.

Recovery, possibly selective, of the metal-containing precipitates obtained by the process according to the invention, with a view to their recycling, is possible.

DESCRIPTION OF FIGURES

For FIGS. 1a and 1b, the culturing condition components which vary as follows: F=presence of formate; E=presence of ethanol; S=presence of sulphate; T=presence of thiosulphate; YE=presence of yeast extract. The different sets of conditions are represented on both figures in the following manner.

Symbols x: E and T;
Symbols ○: E and S;
Symbols +: E, T and YE;
Symbols □: E, S and YE;
Heavy continuous line: F and T;
Dashed line: F and S;
Dotted line: F, T and YE; and
Fine continuous line: F, S and YE.

EXPERIMENTAL SECTION

Bacterial Strains and Culture Media

Two bacterial strains are studied here: *Desulfonatronum lacustre* (pH: 9.5) and *Desulfonatrovibrio hydrogenevorans* (pH: 9.5). Both strains are cultured at 37° C. The energy sources (electron donors) tested are ethanol and formate and the electron acceptors tested are sulphate and thiosulphate. The strains are described in detail in the examples below. The selection of the strains was performed using 5 ml cultures in Hungate tubes.

The composition of the culture medium (called MLF) is as follows (in g/L):

| | |
|---|---|
| $NH_4Cl$ | 1 |
| $K_2HPO_4$ | 0.3 |
| $KH_2PO_4$ | 0.3 |
| $CaCl_2 \cdot 2H_2O$ | 0.1 |
| KCl | 0.1 |
| $MgCl_2 \cdot 6H_2O$ | 0.1 |
| Cysteine | 0.5 |
| $Na_2S$ | 0.04% |
| Widdel trace elements | 1 mL |
| Yeast extract | 0.1 |

The sodium sulphide, the energy source, the electron acceptor and the buffer defined below are added to the medium just before the inoculation of the latter. The sodium sulphide makes it possible greatly to diminish the redox potential of the medium, thus creating conditions favourable to the growth of strictly anaerobic bacteria.

The buffer for the culturing performed at pH 9.5 is 1.6% $Na_2CO_3$.

Fermentation Device

The hydrogen sulphide production tests were performed by culturing of the selected strain in suspension in a "batch" type reactor (CHEMAP A G, Switzerland) of 20 L capacity.

The pH, temperature and stirring speed are regulated in a control box adjacent to the fermenter (reactor). The pH is continuously regulated by means of a pH probe immersed in the culture medium. When a pH value lower than the specified point is detected, a volume of caustic soda or carbonate solution is injected into the fermenter by means of a peristaltic pump.

The temperature of the fermenter (37° C.) is regulated by circulation of thermostatted water through the metal body of the apparatus.

The stirring (15 revolutions/minute) is carried out by a marine type propeller.

The nitrogen feed is regulated by a ball flowmeter. A slight overpressure is maintained in the fermenter by the incoming nitrogen flow and by immersion of the gas outlet in a 1N solution of caustic soda. This caustic soda solution also makes it possible to neutralise gaseous effluxes of $H_2S$ that may be emitted during the fermentation.

A tap located at the bottom of the reactor tank makes it possible to take samples during the fermentation.

To start this, the reactor, containing 10 litres of MLF culture medium and the thiosulphate, is initially sterilised with steam then cooled under a current of nitrogen. The formate and an inoculum of 2 litres of a culture at the end of the exponential growth phase are then injected. The pH is then adjusted by addition of sterile 40 mM carbonate and deoxygenated.

Thereafter, the compounds added to the culture (caustic soda, carbonate, culture MLF medium) are not sterilised or deaerated beforehand.

Monitoring of Growth

The growth of the bacteria is monitored by means of a spectrophotometer by measurement of the optical density of the cultures at a wavelength of 580 nm.

Previously performed studies made it possible to establish a linear relationship between the cell concentration of the bacterium *Thermotoga elfii* (g of dry weight/litre), a thiosulphate-reducing bacterium, and the optical density at 580 nm when the latter does not exceed 0.8: $[Cells]=0.73 \times OD_{580\,nm}$. This method is therefore applied here for the other bacteria.

The presence of precipitates in the cultures of *Desulfonatronum lacustre* imposes a mineralization of these necessary prior to the measurement of the optical density. This mineralization is carried out by addition of 400 μL of 1M persulphuric acid to 4 mL of bacterial culture. After stirring, the mixture is allowed to stand for 2 minutes before reading of the optical density at 580 nm.

Colorimetric Assay of Sulphide

The dosage of dissolved sulphide is performed according to the method of Cord Ruwish (Cord Ruwish R., *J. Microbiol. Methods.* 4: 33-36, 1985): after sampling of 0.1 mL of culture medium, this is rapidly mixed by vortexing with 4 mL of 5 mM $CuSO_4$, 50 mM HCl. The Bordeaux red-coloured copper sulphide thus formed is titrated by measurement of the absorption at 480 nm and comparison with a pre-recorded standard curve.

The dosage of total sulphide is performed by prior basification of the culture medium to pH 12. This results in the dissolution of all of the sulphide which is then titrated as stated above.

Colorimetric Assay of Thiosulphate

The dosage of thiosulphate is performed according to the method described by Nor & Tabatabai (Nor Y. M§ and Tabatabai M. A., *Anal. Lett.* 8: 537-547, 1975): 1 mL of sample is mixed with 1 ml of 0.1M KCN.

$S_2O_3^{2-} \rightarrow SO_3^{2-} + CNS^-$

After 15 minutes, 2 mL of 0.33 M $CuCl_2$ then 1 mL of $Fe(NO_3)_3$—$HNO_3$ are added.

$CNS^- + Fe^{3+} \rightarrow Fe$—$CNS$

The mixture is adjusted to 25 mL with osmosed water, then, after stirring and two minutes wait time, the quantity of sulphur present in the sample is determined by measurement of the absorption of the iron-thiocyanate complex at 460 nm and comparison with a pre-recorded standard curve.

Dosage of Sulphate

The sulphate is titrated according to the method of Tabatabai (Tabatabai M. A., *Sulfur Institut Journal* 10: 11-13, 1974): 1 mL of sample is withdrawn under sterile conditions then acidified with 250 ml of 1N HCl in an Eppendorf tube in order to remove sulphides. The cells are removed by centrifugation (14000 rpm, 3 minutes) and 0.5 mL of supernatant is taken up in 4.5 mL of distilled water. Addition of 250 μL of $BaCl_2$ (1% w/v)-gelatine (0.3% w/v) makes it possible to precipitate the sulphate in the form of barium sulphate. After standing for 30 minutes, the mixture is homogenised on the vortex and the absorption is measured at 420 nm.

The standardisation is performed following the same protocol with 5 mL of distilled water and 250 μL of $BaCl_2$-gelatine solution.

The calibration is carried out on the basis of sulphate standards (1 mM, 5 mM, 10 mM and 20 mM $Na_2SO_4$) to which the above protocol is applied.

Dosage of Sugars, Organic Acids and Alcohols

The dosage of soluble metabolic products is performed by separation by high-pressure liquid phase chromatography (HPLC) on an ORH801 column (Interaction chemicals) with detection with an RID 6A differential refractometer (Shimadzu). The eluent is a filtered (0.65 μm Millipore) 0.005N $H_2SO_4$ solution.

The samples are centrifuged (1300 revolutions.$min^{-1} \times 15$ min) before being injected.

Dosage of Gases

The dosage of gaseous products of the bacterial metabolism is performed by gas phase chromatography (GPC). The chromatograph (Chrompack CP 9000) is equipped with two columns mounted in series (Silicagel GC and Molecular Sieve 5A). Detection is carried out by thermal conductivity using a catharometer. The carrier gas is helium at 2 bars, and the detector filament current is 70 mA. The gas injections (0.1 mL) are performed using a syringe fitted with a valve of the Minimert™ type making it possible to maintain the pressure of the sample.

EXAMPLES

Description of *Desulfonatronum lacustre*

This is a sulphate- and thiosulphate-reducing, alkaliphilic, salt-tolerant and chemolithotrophic bacterium.

Morphology: vibrio, 0.7–0.9×2-3 μm, isolated, in pairs or in spiral chains, mobile by means of a polar flagellum. Gram negative. Multiplication by binary fission. Colony in agar: lenticular, 0.5-2 mm Ø, yellowish then brown, translucent, with whole edge.

Metabolism: non-fermentative

Electron acceptors: sulphate, sulphite, thiosulphate.

Dismutation of thiosulphate to sulphide+sulphate.

Electron donors: $H_2$—$CO_2$, formate, ethanol→acetate.

No growth on acetate, propionate, butyrate, pyruvate, lactate, malate, fumarate, succinate, methanol, glycerol, choline, betaine, casamino acids, yeast extract, glucose, fructose, mannose, xylose or rhamnose.

Syntrophy with *Spirochaeta alcalica* or *Desulfonatronovibrio hydrogenovorans*.

Presence of cyt c, absence of desulphoviridine.

Growth stimulated by yeast extract or acetate.

Physiology: T optimum=37-40° C. (20-45° C.).

pH optimum=9.5 (8-10).

NaCl optimum=0% w/v (0-10% w/v).

Dependent on sodium ions and carbonate.

DNA: 57.3 mol % G+C

RNA 16S sequence: Y14594

Typical strain Z-7951 (DSM 10312).

Origin: sediment from Lake Khadyn.

Reference: Pikuta E V, Zhilina T N, Zavarzin G A, Kostrikina N A, Osipov G A, Rainey F A (1998) *Desulfonatronum*

*lacustre* gen. nov., sp. nov., a new alkaliphilic sulphate-reducing bacterium utilizing ethanol. Microbiology (Engl. Tr. Mikrobiologiya) 67, 123-131.

Description of *Desulfonatrovibrio hydrogenevorans*

Sulphate- and thiosulphate-reducing, alkaliphilic, weakly halophilic bacterium.

Morphology: *vibrio*, 0.5×1.5-2 µm, 1 polar flagellum, filamentous appendages, isolated or in pairs or in short chains, Gram negative.

Metabolism: lithoheterotrophic

Electron acceptors: sulphate, sulphite, thiosulphate.

Electron donors: $H_2+CO_2$, formate.

Carbon sources: acetate with yeast extract or vitamins.

Formation of sulphide on dimethyl sulphoxide with no growth.

Growth inhibited by sulphur.

Disproportionation of thiosulphate to sulphate and sulphide.

No desulphoviridine.

Physiology: alkaliphilic weakly halophilic

T optimum: 37° C. (15-43° C.)

pH optimum: 9.5-9.7 (8-10.2)

NaCl optimum: 3% (1-12%)

$t_{1/2}$ optimum=26.5 hrs on sulphate, 20.1 hr on thiosulphate.

Dependent on $Na^+$

DNA: 48.6 mol % G+C (Tm)

RNA 16S sequence: X99234

Typical strain: Z-7935T (DSM 9292 T).

Origin: sediments of alkaline lakes (equatorial Lake Magadi)

Reference: Zhilina T N, Zavarzin G A, Rainey F A, Pikuta E N, Osipov G A, Kostrikina N A (1997) *Desulfonatronovibrio hydrogenovorans* gen. nov., sp. nov., an alkaliphilic, sulphate-reducing bacterium. Int. J. Syst. Bacteriol. 47, 144-149.

Determination of the Optimal Culture Conditions for the Production of Hydrogen Sulphide by *Desulfonatronum lacustre*

Figure 1A:
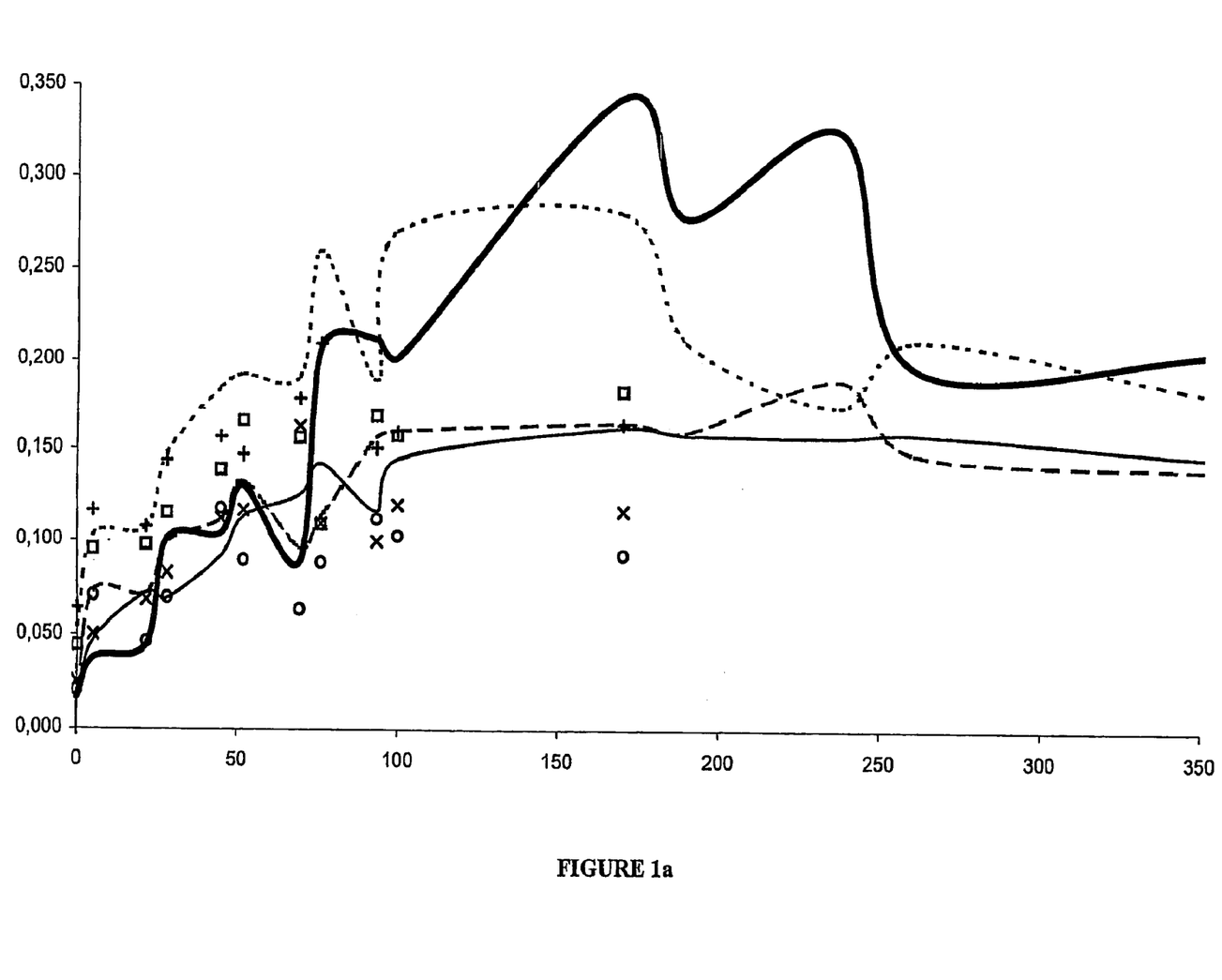
FIG. 1a represents the growth of a culture of *Desulfonatronum lacustre* under different culturing conditions. The x axis shows the time in hours. The y axis shows the optical density measurement at 580 nm.
Figure 1B:
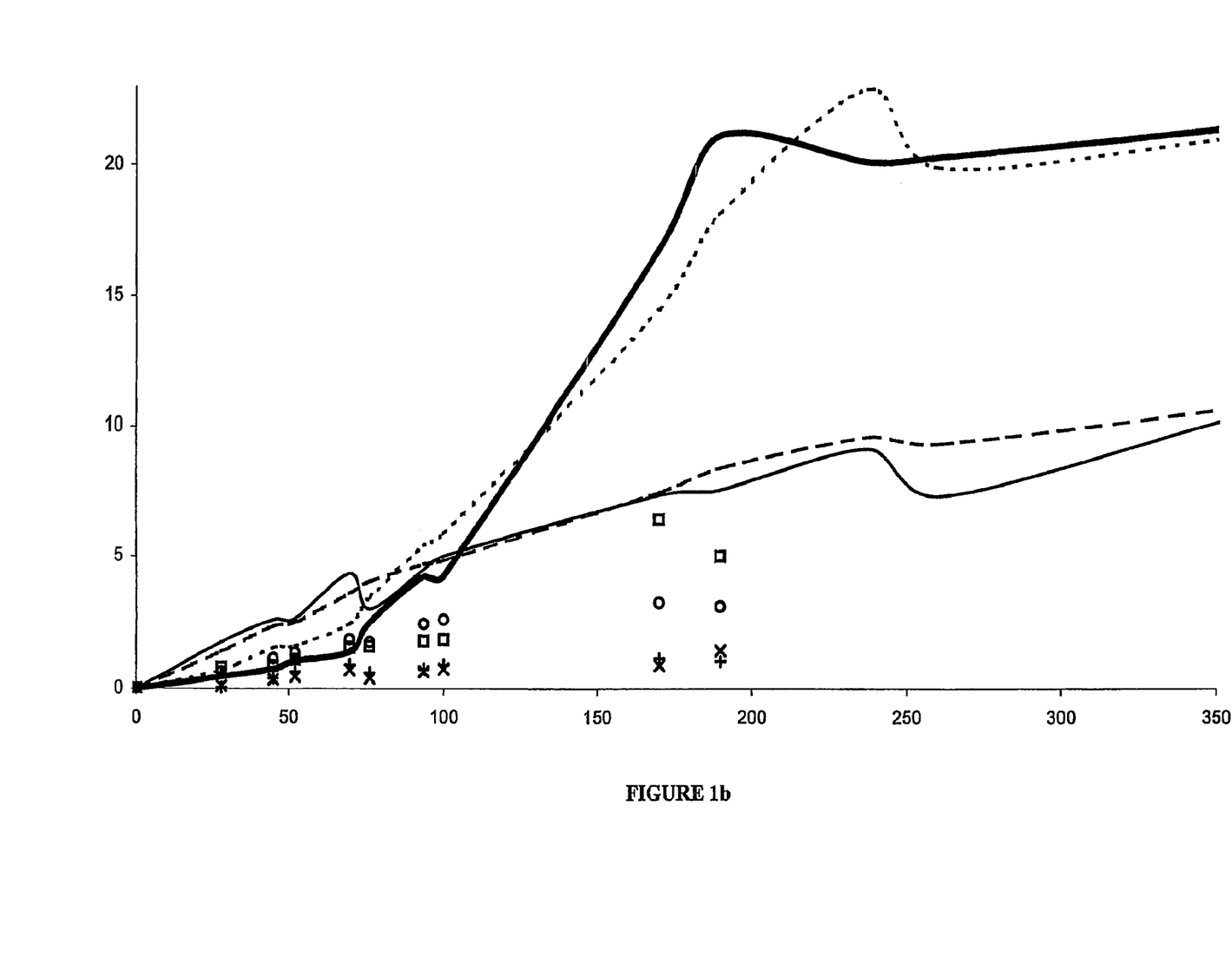
FIG. 1b represents the production of dissolved hydrogen sulphide during culturing of *Desulfonatronum lacustre* under different culturing conditions. The x axis shows the time in hours. The y axis shows the concentration of HS$^-$ in mM.

Reference is made here to FIG. 1*a*, which represents the measurement of the optical density with the passage of time, which is directly related to the concentration of the bacteria, as a function of time; and to FIG. 1*b*, which represents the measurement of the concentration of dissolved hydrogen sulphide as a function of time.

Different culture conditions are tested:

F: presence of formate; E: presence of ethanol; S: presence of sulphate; T: presence of thiosulphate; YE: presence of yeast extract (Panreac, Spain).

The experiments were performed in duplicate. FIGS. 1*a* and 1*b* represent the mean of the results derived from the measurements of the OD at 580 nm and of the hydrogen sulphide dosage for the different cultures.

Examination of these results shows that:

the use of formate makes it possible to obtain higher concentrations of hydrogen sulphide than the use of ethanol;

cultures in the presence of thiosulphate make it possible to obtain higher concentrations of hydrogen sulphide than in the presence of sulphate;

the addition of yeast extract to the culture medium does not make it possible to obtain results significantly different from those obtained without that addition; the reason for this is that yeast extract is present in trace amounts in the inoculum of bacteria;

*Desulfonatronum lacustre* reduces thiosulphate by oxidation of formate producing high concentrations (about 22 mM) of hydrogen sulphide;

the rate of production of hydrogen sulphide is 0.122 mM/hr.

*Desulfonatronum lacustre* is thus suitable for the production of hydrogen sulphide and was retained for the continuation of the experiments owing to:

its ability to produce high concentrations of hydrogen sulphide;

its rate of production of hydrogen sulphide;

its alkaliphilia enabling greater solubility of the hydrogen sulphide and a selection pressure for maintenance of the strain in culture. The high pH values eliminate exogenous contamination problems.

Production of Hydrogen Sulphide by *Desulfonatronum lacustre* in "Batch" Reactor 1. Importance of Carbonate for Growth The implementation of the first cultures of *Desulfonatronum lacustre* in a batch reactor made it possible to confirm the dependence of this strain on carbonate. In fact, in the absence of sodium carbonate in the culture medium, no growth of this bacterium was observed for a week. The addition of a concentration of sodium bicarbonate less than 16.6 g/l does not enable growth either. It has been postulated that carbonate is involved in the dissociation equilibrium of formate via the $CO_2$ concentration of the gaseous phase.

2. Growth and Production at pH 9.5

A culture of *Desulfonatronum lacustre* was carried out in the first instance by inoculation of 10 litres of medium with an inoculum consisting of two litres of a culture at the end of the exponential growth phase. The energy source is represented by formate (74 mM) and the terminal electron acceptor is thiosulphate (20 mM). The adjustment of the pH to 9.5 is initially performed with sodium carbonate. The pH is then regulated by injection of 4N caustic soda solution. The results of the experiment are shown on FIG. 2*a*.

Figure 2A:
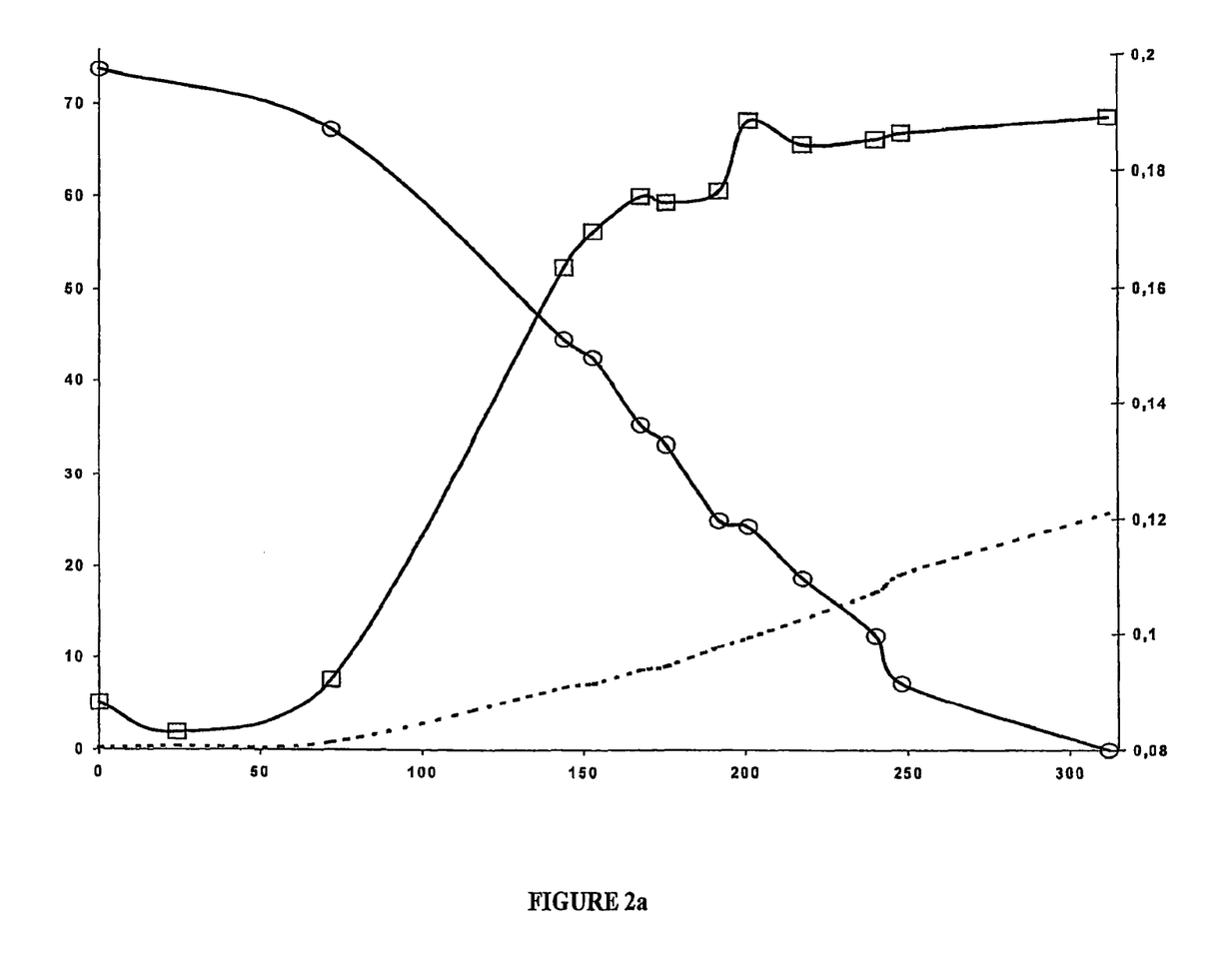
FIG. 2a represents the result of culturing *Desulfonatronum lacustre* in a "batch" type reactor at pH 9.5. The change in the concentration of hydrogen sulphide is represented by a dotted line; that of the concentration of formate is represented as a continuous line with ○ symbols and that of the optical density at 580 nm (indicative of the concentration of bacteria) is represented as a continuous line with □ symbols. The x axis corresponds to the time in hours. The left-hand y axis corresponds to the concentrations in mM (for hydrogen sulphide and formate); and the right-hand y axis corresponds to the OD at 580 nm.

The growth of *Desulfonatronum lacustre* follows a typical curve of sigmoidal shape: after a latency phase (t<50 hrs), the bacteria enter a phase of exponential growth (50 hrs<t<200 hrs), then retardation phase appears (t>200 hrs). A stationary phase is observed from t=200 hrs. The formate being monitored in real time, the energy source was replenished for a second series of experiments at pH 9.5 after its concentration reached 0 mM.

The optical density of the culture is remarkably low and only increases very slightly on addition of formate: a growth limitation seems to be in operation. The generation time of *Desulfonatronum lacustre* under the experimental conditions is 71.45 hrs at pH 9.5. This value is remarkable, even for a thiosulphate-reducing bacterium. By comparison, the generation time of *Desulfonatronum lacustre* under the same experimental conditions (medium, formate, thiosulphate, yeast extract, temperature, pH) but during its culturing in a Hungate tube (5 mL of medium) is 84.52 hrs. It thus appears that culturing in a fermenter where stirring and continuous regulation of the pH are maintained and where the liquid volume/gas volume ratio is higher makes it possible to decrease the generation time of this bacterium.

Observation of the consumption of formate shows that this is correlated with the bacterial growth. Low during the initial latency phase, the consumption of formate increases during the exponential growth phase then slows during the stationary phase. However, it is noted that the consumption of formate is maintained, which is consistent with the observation of the maintenance of hydrogen sulphide production activity by the bacteria in the stationary state.

By correlation between the quantity of formate consumed and that of hydrogen sulphide produced, it is deduced that under the experimental conditions the formation of one mole of hydrogen sulphide requires the oxidation of 2.83 moles of formate at pH 9.5.

After establishment of a biomass inside the reactor and exhaustion of the energy source, a correlation was established between the optical density of the culture at 580 nm and the biomass. Thus for an $OD_{580\,nm}$ of 0.465, a dry weight of 67.6 mg/L was determined. Assuming that the relationship biomass=ft($OD_{580\,nm}$) is linear, we have:

Biomass (mg/L)=145.37×$OD_{580\,nm}$

It was possible to determine the specific rate of production of hydrogen sulphide. The specific rate of production of hydrogen sulphide at pH 9.5 under the experimental conditions is 3.318 mmol $HS^-$ $g^{-1}$ $hr^{-1}$.

3. Growth and Production at pH 10

Growth of *Desulfonatronum lacustre* was then carried out at pH 10 by addition of concentrated culture medium to the reactor and alteration of the specified value for the pH. The results of this experiment are presented in FIG. 2*b*. At t=92 hrs, the culture medium was enriched by addition of 1 L of concentrated culture medium (equivalent to 8 litres of standard medium) in order to replenish the energy source the concentration of which was decreasing markedly. This addition caused a decrease in the concentration of hydrogen sulphide and a decrease in the $OD_{580\,nm}$.

Figure 2B:
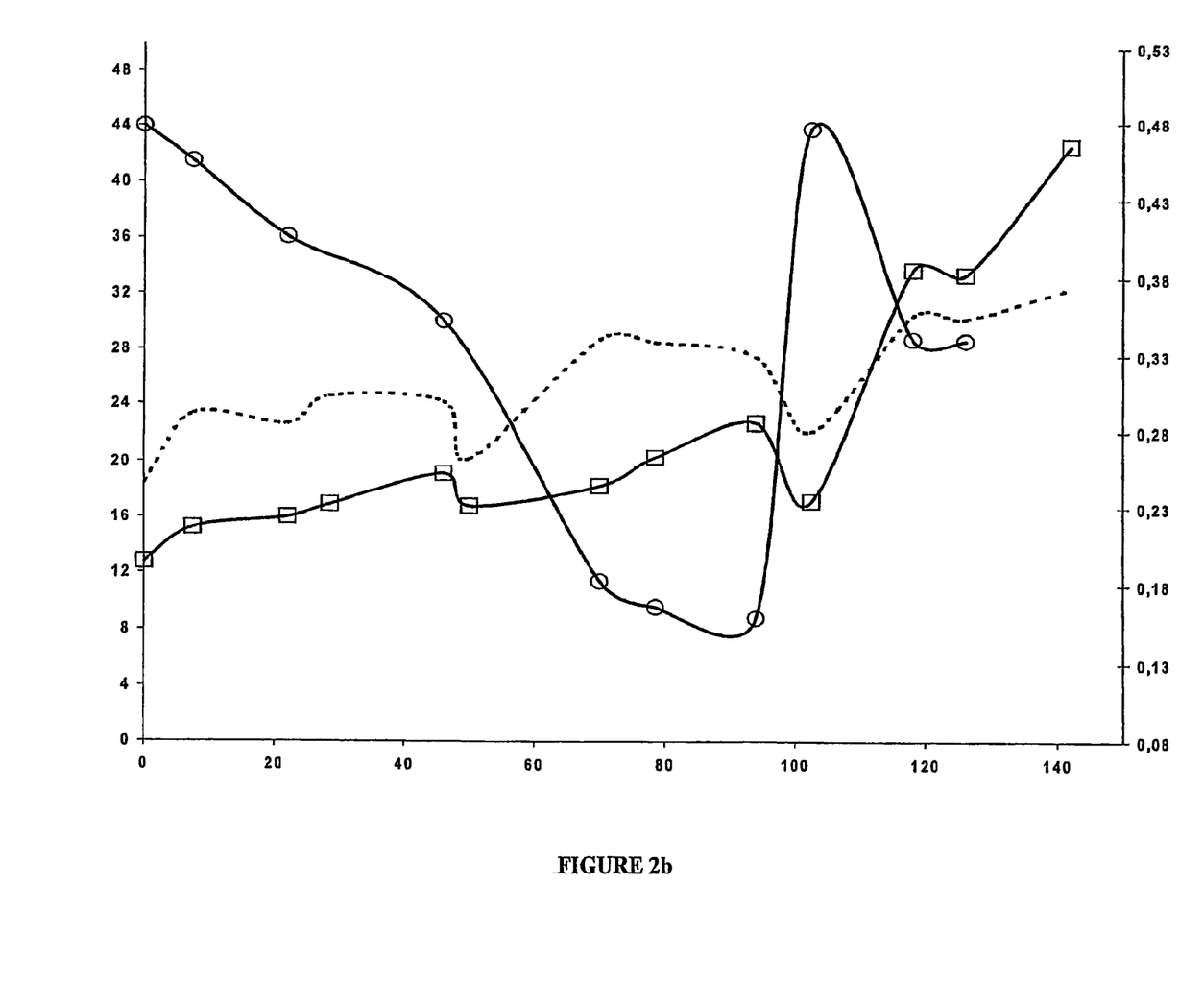
FIG. 2b represents the result of culturing *Desulfonatronum lacustre* in a "batch" type reactor at pH 10. The change in the concentration of hydrogen sulphide is represented by a dotted line; that of the concentration of formate is represented as a continuous line with ○ symbols and that of the optical density at 580 nm (indicative of the concentration of bacteria) is represented as a continuous line with □ symbols. The x axis corresponds to the time in hours. The left-hand y axis corresponds to the concentrations in mM (for hydrogen sulphide and formate); and the right-hand y axis corresponds to the OD at 580 nm. It should be noted that at t=92 hrs an injection of concentrated medium is performed (see corresponding example below).

It can be observed that the growth of *Desulfonatronum lacustre* is maintained at pH 10. This is still correlated with the oxidation of the energy source, the formate. It is however more than twice as slow as at pH 9.5. In fact the generation time of *Desulfonatronum lacustre* under our experimental conditions is 141.45 hrs at pH 10.

It can be noted that the concentration of hydrogen sulphide can attain the value of 32 mM. This high concentration of sulphide can be the cause of the decrease in the rate of growth of *Desulfonatronum lacustre*. This strain can however be considered exceptionally tolerant to sulphides in view of the concentrations of hydrogen sulphide encountered in the culture medium.

By correlation between the quantity of formate consumed and that of hydrogen sulphide produced, we deduce that increasing the pH of the culture medium to a value of 10 does not change the energy yield of the formation of hydrogen sulphide. In fact, the values at pH 9.5 and pH 10 are almost identical: the formation of one mole of hydrogen sulphide requires the oxidation of 2.66 moles of formate at pH 10.

However, the specific rate of production of hydrogen sulphide decreases slightly (11%) with the change in the pH from 9.5 to 10. The specific rate of production of hydrogen sulphide at pH 10 under our experimental conditions is 2.974±0.635 mmol $HS^-$ $g^{-1}$ $hr^{-1}$.

This decrease in the activity of *Desulfonatronum lacustre* with the change from pH 9.5 to pH 10 is not in agreement with the results of Pikuta et al. who observed a 50% decrease in the sulphidogenic activity of this strain with the change from pH 9.5 to pH 10.

During culturing performed at pH 10, the medium added to the reactor was neither sterilised nor deaerated. Microscopic examination made it possible to check that only *Desulfonatronum lacustre* was able to maintain itself under its growth-restrictive conditions (high pH, inorganic medium, high concentration of sulphides). Further, the high concentration of sulphides in the reactor makes it possible to maintain complete absence of oxygen therein, as is shown by the maintenance of a high concentration of hydrogen sulphide.

Optimisation of the Culture Medium

Cultures were performed in Hungate tubes in different culture media derived from the standard culture medium MLF. Depending on the culture series, the cysteine, the sodium sulphide, the acetate, the yeast extract or the trace elements were omitted. The first inoculation of *Desulfonatronum lacustre* was performed from a pre-culture on rich MLF medium. Thereafter, for the second (t=10 days) and third (t=20 days) subcultures, the inoculum was provided by the culture previously performed on the same type of medium. These subcultures in series make it possible to ensure the absence of the desired compound through the effect of the dilutions.

It should be recalled that in the medium MLF, the cysteine and the sodium sulphide are added as reducing agents making it possible to favour the establishment of a low redox potential favourable to the growth of *Desulfonatronum lacustre*. The acetate is added to provide a complementary source of carbon readily available to the bacterial strain, which should allow it to initiate its growth. The yeast extract is a source of amino acids and of inorganic growth factors for this heterotrophic strain and the solution of Widdel trace elements provides many metals that may be involved in the bacterial metabolism.

The results derived from the third subculturing of the different alternative culture media are shown in Table 1 below. From the comparison of these results, it can be noted that the three lowest growths and the three lowest hydrogen sulphide production levels are correlated with the absence of yeast extract (media B, D and I).

A low concentration of yeast extract (0.1 g/L) appears indispensable for good growth of *Desulfonatronum lacustre* and high production of hydrogen sulphide by this strain. To a lesser extent, the omission of the solution of Widdel trace elements appears to limit the production of hydrogen sulphide by *Desulfonatronum lacustre*. The role of these trace elements can be explained by the presence of metals in the haems of the enzymes involved in the sulphate respiration in the sulphate-reducing bacteria. These elements could be supplied by the impurities encountered in products of industrial quality and which are not found in the products of "analytical" quality used in the laboratory.

TABLE 1

| Compounds | Concentrations (mg/l) | A | B | C | D | E | F | G | H | I |
|---|---|---|---|---|---|---|---|---|---|---|
| Cysteine | 0.5 | X | X | X | X |   | X |   | X |   |
| Sodium sulphide | 0.4 | X | X | X | X | X |   | X |   |   |
| Sodium acetate | 0.16 (2 mM) | X | X |   |   | X | X |   |   |   |
| Yeast extract | 0.1 | X |   | X |   | X | X | X |   | X |

TABLE 1-continued

| Compounds | Concentrations (mg/l) | A | B | C | D | E | F | G | H | I |
|---|---|---|---|---|---|---|---|---|---|---|
| Widdel trace elements | 1 ml | | X | | X | X | X | X | X | |
| Results of 3rd subculturing* | $OD_{580\,nm}$ | 0.23 | 0.18 | 0.25 | 0.18 | 0.3 | 0.22 | 0.23 | 0.24 | 0.2 |
| | $HS^-$ | 9.35 | 6.45 | 10.5 | 2.35 | 14 | 10.9 | 8.85 | 12.5 | 1.9 |

*the results are the mean of two series of experiments.

Precipitation of Copper by Hydrogen Sulphide

The dosage of the dissolved hydrogen sulphide is performed by measurement of the absorbance of the Bordeaux red-coloured copper sulphide formed by the action of the hydrogen sulphide on copper sulphate. The reaction involved in this dosage was exploited to illustrate the capabilities of hydrogen sulphide for the separation of dissolved metals in an effluent.

The copper sulphide is formed instantaneously on mixing of the hydrogen sulphide and the dissolved copper with stirring. The copper sulphide thus formed precipitates rapidly, in a manner visible to the naked eye. When the mixture is allowed to stand for 5 minutes, the major part of the precipitate is found at the bottom of the test-tube.

The addition of a coagulant such as $FeCl_3$ makes it possible to precipitate the whole of the copper. The precipitation of metals in the form of sulphides by the use of the hydrogen sulphide present in cultures of sulphate- and thiosulphate-reducing bacteria has been confirmed.

Decontamination of an Industrial Effluent

A precipitation of heavy metals contained in an actual industrial effluent provided by the company X, situated in the Vaucluse and confronted with contamination of its effluents with the lead which it converts in the context of its activity of accumulator production, is performed.

*Desulfonatronum lacustre* is cultured at 37° C. for more than 2 months in 2 litres of MLF medium. The initial pH of the culture is 9.5. The energy source utilised is formate, and the sulphur source is thiosulphate.

The polluted effluent is drawn off upstream of the currently existing treatment works.

A measurement of the concentration of hydrogen sulphide is first preformed. After dilution of the culture medium to ¼, the measurement gives a concentration of 4×12.9=51.6 mM. This exceptional concentration of hydrogen sulphide in a culture medium is due to a particularly long culturing time (greater than 60 days).

Analysis of the final pH of the medium shows that this is 8.8. The fall in the pH from 9.5 to 8.8 in spite of the presence of a carbonate buffer confirms the generation of a large quantity of acid during the culturing of *Desulfonatronum lacustre*.

This concentration of hydrogen sulphide greater than 50 mM in the culture medium shows that *Desulfonatronum lacustre* is capable of tolerating particularly high concentrations of sulphides.

5 ml of culture medium containing 51.6 mM of hydrogen sulphide are withdrawn by means of a syringe and injected into 150 ml of contaminated effluent. The effluent before injection is shown on photo A in FIG. 3, and the effluent immediately after injection is shown on photo B in FIG. 3.

Figure 3:
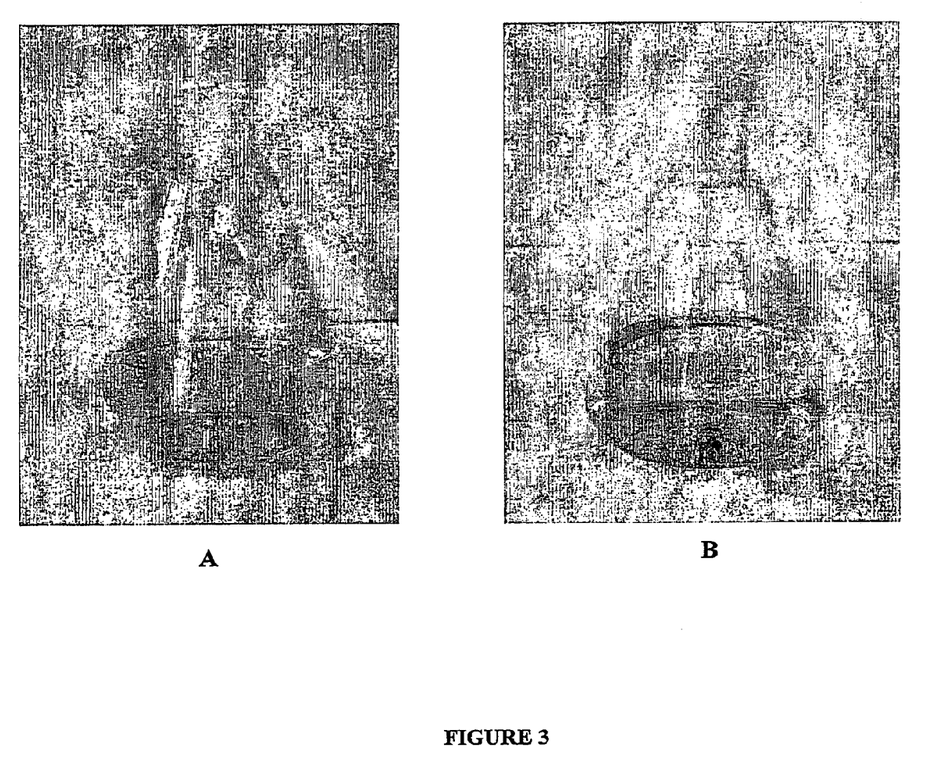
FIG. 3 represents the result of a heavy metals precipitation experiment according to the invention. Photo A represents a sample of 150 ml of industrial effluent essentially containing dissolved lead. Photo B represents the same sample immediately after injection of 5 ml of culture medium obtained after 60 days of culturing of *Desulfonatronum lacustre*, containing more than 50 mM of hydrogen sulphide. Black particles of lead sulphide are visible.

Following the injection of the hydrogen sulphide into the effluent, particles of lead sulphides, identified by the characteristic lustrous black colour, appear and rapidly sediment.

The injection of culture medium containing hydrogen sulphide produced by the metabolism of *Desulfonatronum lacustre* thus makes it possible instantaneously to effect the precipitation of the lead and its separation from the industrial effluent.

The invention claimed is:

1. A process for the decontamination of an effluent containing one or more dissolved metals, the process comprising:
   (i) producing hydrogen sulphide in a form largely soluble in an aqueous medium comprising the following stages:
   a stage of culturing alkaliphilic sulphate-reducing or thiosulphate reducing bacteria selected from at least one species of the Desulfohalobiaceae family or of the *Desulfonatronum* genus, or of which the gene coding for the ribosomal RNA 16 S exhibits a homology of at least 97% with the corresponding gene of any one of the species of the Desulfohalobiaceae family or of the *Desulfonatronum* genus, in the presence of an organic compound serving as an electron donor, and in the presence of a sulphurous compound serving as an electron acceptor, which leads to the formation of hydrogen sulphide, and
   a sequence of the following two stages:
   a first stage in which the culturing of the bacteria is carried out under conditions appropriate for the growth of the bacteria and for the concomitant production of hydrogen sulphide, and
   a second stage in which the culturing of the bacteria is carried out under conditions appropriate for the production of hydrogen sulphide in the absence of growth of the said bacteria, and
   optionally repeating the sequence of the stages constituting one cycle several times if necessary;
   (ii) contacting the effluent with the hydrogen sulphide; and
   (iii) reducing the one or more dissolved metals and/or precipitating the one or more dissolved metals in the form of metal sulphides.

2. The process according to claim 1, wherein said contacting the effluent with the hydrogen sulphide is carried out at a pH in a range of from 2 to 12.

3. The process according to claim 1, wherein said contacting the effluent with the hydrogen sulphide is carried out at a pH in a range of from about 7 to 12.

4. The process according to claim 1, wherein producing the hydrogen sulphide is carried out in a culturing tank, and contacting the effluent with the hydrogen sulphide is carried out in a reaction tank, the culturing tank and the reaction tank being separate tanks, and
   between the producing hydrogen sulphide step and the contacting the effluent with the hydrogen sulphide step, the process further comprises injecting all or part of the hydrogen sulphide produced in the culturing tank into the reaction tank.

5. The process according to claim 4, wherein no fraction of the effluent is injected into the culturing tank.

6. The process according to claim 4, wherein a fraction of the effluent is injected into the culturing tank.

7. The process according to claim 4, wherein contacting the effluent with the hydrogen sulphide in the reaction tank is carried out in the absence of a gaseous phase and in such a manner that there is no release of gaseous hydrogen sulphide.

8. The process according to claim 4, further comprising:
measuring the concentration of hydrogen sulphide produced in the culturing tank;
estimating the concentration of the one or more dissolved metals in the effluent to be decontaminated; and
adjusting the quantity of hydrogen sulphide to be injected into the reaction tank based on the result of said measuring and of said estimating.

9. The process according to claim 1, wherein the one or more dissolved metals is selected from the group consisting of copper, zinc, arsenic, cadmium, chromium, tin, manganese, mercury, nickel, and lead.

10. The process according to claim 1, wherein the organic compound serving as an electron donor is formate and the sulphurous compound serving as an electron acceptor is thiosulphate.

11. The process according to claim 1, wherein the culturing of the alkaliphilic sulphate-reducing or thiosulphate-reducing bacteria is carried out at a pH greater than or equal to 9.

12. The process according to claim 1, wherein the culturing of the alkaliphilic sulphate-reducing or thiosulphate-reducing bacteria is carried out at a pH greater than or equal to 9.5.

13. The process according to claim 1, wherein the culturing of the alkaliphilic sulphate-reducing or thiosulphate-reducing bacteria is carried out at a pH greater than or equal to 10.

14. The process according to claim 1, wherein the bacteria have a tolerance to hydrogen sulphide, and the bacteria tolerate concentrations of hydrogen sulphide at least greater than 20 mM.

15. The process according to claim 1, wherein the bacteria belong to the species *Desulfonatronum lacustre*.

16. The process according to claim 1, wherein the bacteria belong to the species *Desulfonatronovibrio hydrogenevorans*.

17. The process according to claim 1, wherein the culturing is carried out on a support suitable for the growth of the bacteria, leading to the formation of a biofilm.

18. The process according to claim 1, wherein the passage from one stage to the other for producing hydrogen sulphide is carried out by addition of one or several acidic or basic chemical substances resulting in a change in the pH of the culture medium of the bacteria.

19. The process according to claim 1, wherein the first stage is carried out at a pH ranging from 9 to 10 and the second stage is carried out at a pH greater than 10.

20. The process according to claim 1, wherein the hydrogen sulphide is produced at a concentration greater than or equal to 10 mM.

21. The process according to claim 1, wherein the hydrogen sulphide is produced at a concentration greater than or equal to 20 mM.

22. The process according to claim 1, wherein the hydrogen sulphide is produced at a concentration greater than or equal to 30 mM.

23. The process according to claim 1, wherein the bacteria belong to the species *Desulfonatronum lacustre*, the organic compound serving as an electron donor is formate, the sulphurous compound serving as an electron acceptor is thiosulphate and the bacteria are continuously cultured on a biofilm at a pH greater than 10.

* * * * *